United States Patent
Cocheteux et al.

(10) Patent No.: US 8,490,790 B2
(45) Date of Patent: Jul. 23, 2013

(54) PLATE FOR HOLDING A GROUP OF SYRINGE BODY OBJECTS

(75) Inventors: Bruno Cocheteux, Voiron (FR); Lionel Vedrine, Ridgewood, NJ (US)

(73) Assignee: Becton Dickinson France S.A.S., Le Pont de Claix (FR)

( * ) Notice: Subject to any disclaimer, the term of this patent is extended or adjusted under 35 U.S.C. 154(b) by 926 days.

(21) Appl. No.: 10/546,673

(22) PCT Filed: Feb. 24, 2003

(86) PCT No.: PCT/FR03/00593
§ 371 (c)(1),
(2), (4) Date: Jun. 9, 2006

(87) PCT Pub. No.: WO2004/082745
PCT Pub. Date: Sep. 30, 2004

(65) Prior Publication Data
US 2007/0151882 A1   Jul. 5, 2007

(51) Int. Cl.
*B65D 83/10* (2006.01)
(52) U.S. Cl.
USPC ............ 206/366; 206/364; 206/563; 206/560
(58) Field of Classification Search
USPC ................ 206/369, 363–366, 560, 562, 563, 206/477, 504, 509; 211/74; 422/562, 566; 494/16; 220/23.4, 23.8
See application file for complete search history.

(56) References Cited

U.S. PATENT DOCUMENTS

| | | | | |
|---|---|---|---|---|
| 2,523,877 A * | 9/1950 | Pestolesi | ........................ | 206/366 |
| 3,876,067 A * | 4/1975 | Schwarz | ........................ | 206/205 |
| 4,729,208 A * | 3/1988 | Galy et al. | ........................ | 53/432 |
| 4,919,264 A * | 4/1990 | Shinall | ........................ | 206/210 |
| 5,322,668 A * | 6/1994 | Tomasso | ........................ | 211/74 |
| 5,338,309 A * | 8/1994 | Imbert | ........................ | 604/187 |
| 5,470,536 A * | 11/1995 | Jarvimaki | ........................ | 422/102 |
| 6,019,225 A * | 2/2000 | Kalmakis et al. | ........................ | 206/563 |
| 6,106,783 A | 8/2000 | Gamble | | |
| 6,149,872 A * | 11/2000 | Mack et al. | ........................ | 206/509 |
| 6,161,696 A * | 12/2000 | Lashley | ........................ | 206/477 |
| 6,164,044 A * | 12/2000 | Porfano et al. | ........................ | 53/471 |
| 6,189,292 B1 * | 2/2001 | Odell et al. | ........................ | 53/425 |
| 6,213,296 B1 * | 4/2001 | Streich et al. | ........................ | 206/373 |
| 6,216,885 B1 * | 4/2001 | Guillaume | ........................ | 211/85.13 |
| 6,286,678 B1 * | 9/2001 | Petrek | ........................ | 206/443 |

(Continued)

FOREIGN PATENT DOCUMENTS

| | | |
|---|---|---|
| EP | 0790063 A | 8/1997 |
| EP | 0976453 A | 2/2000 |
| WO | 0211797 A | 2/2002 |

OTHER PUBLICATIONS

International Search Report dated May 11, 2003.

*Primary Examiner* — Andrew Perreault
(74) *Attorney, Agent, or Firm* — Cozen O'Connor

(57) ABSTRACT

A plate with housings for receiving objects for bulking, each housing being delimited by lateral walls and comprising a support zone for receiving the object for bulking. Each housing is formed by a cell with the lateral walls delimiting the cells adjoining one another from one cell to an adjacent cell and extending in a direction substantially perpendicular to the plane of the plate. Each cell is shaped to at least partially receive the proximal part of an object for bulking and each cell immobilizes each object for bulking.

17 Claims, 3 Drawing Sheets

U.S. PATENT DOCUMENTS

| | | | |
|---|---|---|---|
| 6,566,144 B1 * | 5/2003 | Madril et al. | 436/177 |
| 6,719,141 B2 * | 4/2004 | Heinz et al. | 206/563 |
| 2001/0052476 A1 * | 12/2001 | Heinz et al. | 206/443 |
| 2001/0056265 A1 | 12/2001 | Heinz et al. | |
| 2002/0014430 A1 | 2/2002 | Groth | |

* cited by examiner

PLATE FOR HOLDING A GROUP OF SYRINGE BODY OBJECTS

PRIORITY CLAIM

This is a U.S. national stage of application No. PCT/FR03/00593, filed on 24 Feb. 2003.

BACKGROUND OF THE INVENTION

The present invention relates to an assembly of elements for bulking elongate objects, particularly syringe bodies.

DESCRIPTION OF THE PRIOR ART

Syringe bodies are frequently manufactured at one site and filled at another site, which involves transportation of these syringe bodies from one site to another.

For this transportation, and in order to prevent any damage to the syringe bodies, it is common to bulk the syringe bodies on a plate with shafts for receiving the syringe bodies, and then to place the assembly in a packing box, this box then being sealed and sterilized. At the destination, the box is opened and then the plate is removed from this box, it being possible for this plate to be used for handling the syringe bodies and filling them using automated means.

A known bulking plate, used in this specific application, comprises a base plate in which is formed a plurality of shafts projecting from one face of this base plate, these shafts being sized in order to receive the syringe bodies through them until the proximal collars of the syringe bodies come to bear against the upper free edges of these shafts.

A plate of this type has the drawback that it is not very rigid, which limits its dimensions and thus the number of syringe bodies it is possible to place in one and the same box. This lack of rigidity may also have detrimental consequences on the automated or manual operations of handling the plates, of engaging or removing the plates in or from the packing boxes, and of filling the syringe bodies.

Moreover, the syringe bodies are not immobilized relative to the plate either in the direction of their longitudinal axis or in terms of pivoting about that axis. The lack of axial immobilization limits the potential ways in which the packing box may be handled, during operations of sterilizing/decontaminating said box, or the possible storage positions of this box, or requires the syringe bodies to be held relative to the plate during handling or when in storage positions involving overturning of the box. The possible storage positions or ways in which the plate may be handled before or after it has been placed in this box are also limited in the same way. The lack of immobilization in terms of pivoting requires the provision of sufficient distance between two adjacent shafts so that the collars of the syringe bodies received in these two shafts, when these collars are non-circular, do not come into contact with one another, which could damage them or generate particles. The result of this is a limitation on the number of syringe bodies it is possible to accommodate on a plate of given dimensions.

Moreover, the existing plate does not allow the placing on the syringe bodies of proximal support hold pieces to facilitate the support holding by the user's fingers when carrying out an injection. In point of fact, it would be advantageous to be able to place such proximal support hold pieces on the syringe bodies before filling of these syringe bodies, while fully protecting these proximal support hold pieces during transportation of the syringe bodies.

SUMMARY OF THE INVENTION

The present invention aims to remedy these drawbacks.

Its principal object is thus to provide an assembly of elements for bulking elongate objects, particularly syringe bodies, that includes a bulking plate that has significant rigidity so as to ensure perfect holding of the objects for bulking, without detrimental consequences for automated or manual handling of the plate and without an awkward restriction in terms of the dimensions that it is possible to give to this plate.

Another object of the invention is to provide an assembly of elements for immobilizing the objects for bulking, particularly syringe bodies, relative to the bulking plate, both in the direction of their longitudinal axis and in terms of pivoting about that axis.

A supplementary object of the invention is to provide an assembly of elements allowing the placing on the syringe bodies, before filling, of proximal support hold pieces as described above, while fully protecting these proximal support hold pieces during transportation of the syringe bodies.

The assembly of elements in question comprises, in a manner known per se, a plate with housings for receiving the objects for bulking, each housing being delimited by lateral walls and comprising a support zone for receiving the object for bulking.

According to the invention,
 each housing is formed by a cell;
 the lateral walls delimiting the cells adjoin one another from one cell to an adjacent cell and extend in a direction substantially perpendicular to the plane of the plate;
 each cell is shaped in order to at least partially receive in it the proximal part of an object for bulking; and
 each cell comprises at least one means for immobilizing each object for bulking.

The fact that the lateral walls are adjoining enables these walls to form continuous lines for stiffening the plate, giving it a rigidity that is well adapted to handling of the plate using, inter alia, automated means. Reception of the proximal parts of the objects for bulking in the cells fully protects these proximal parts, and immobilizing the objects for bulking relative to the plate prevents any risk of damage to one object by another, despite the contiguous nature of the cells.

The assembly of elements may be used for bulking syringe bodies and may therefore comprise, in addition to said plate, support hold pieces for placing on the proximal ends of the syringe bodies, or integral therewith, in order to form surfaces for the support holding of the user's fingers when carrying out an injection, each cell having dimensions that correspond at least partially to those of one of these support hold pieces and each support hold piece being shaped in order to interact with the immobilization means of each cell.

The assembly of elements thus allows assembly of the plate and of these support hold pieces, and the engagement of one support hold piece in a cell is achieved in a precise manner.

The lateral walls delimiting the cells may be slightly flared in order to form a cell entry having dimensions greater than those of a support hold piece.

These cell entries make it possible to guide each support hold piece during its engagement in a cell.

Each support hold piece may be held on a syringe body before the placing of this syringe body in a cell of the plate. Each support hold piece may also be shaped so that it is possible for it to be placed in a cell of the plate and for it to receive the syringe body after said placing.

According to a possible embodiment of each support hold piece in this second case, each support hold piece comprises an opening for the engagement of a syringe body and a series of fingers arranged radially in this opening, these fingers being shaped in order to grip the syringe body between them, with flexing, when this syringe body is engaged in said opening, in order to assemble the support hold piece and the syringe body.

Preferably, each immobilization means consists of at least one snap-fitting tooth provided in a zone of a lateral wall delimiting the cell.

These teeth make it possible to immobilize the objects for bulking after simple insertion of these objects in the cells, but immobilization is reliable.

According to a possible embodiment of the invention in this case, a wall delimiting two adjacent cells comprises a recess provided in its thickness, from the section of this wall, this recess forming two separate snap-fitting teeth, one for each of these cells.

According to another possible embodiment of the invention in this same case, a wall delimiting two adjacent cells comprises a notch in which there is a single snap-fitting tooth, this snap-fitting tooth comprising two snap-fitting projections on its two opposite faces, one for each of these cells.

Each cell preferably has a square or rectangular shape such that the lateral walls delimiting the cells form mutually perpendicular stiffening lines, giving the plate significant rigidity in the directions of these stiffening lines.

Each cell thus advantageously comprises two immobilization means arranged on two opposite sides of the cell, and particularly, when the cell is rectangular, on the smaller sides of this rectangular cell.

These two spaced immobilization means fully hold the syringe body relative to the plate.

Each support zone may consist of at least one wall forming a rim extending inside the cell.

The plate may comprise zones allowing or promoting its gripping. These may, in particular, be walls extending substantially in the plane of the plate, these walls forming surfaces on which vacuum suction cups equipping a machine for handling the plate may be applied.

Preferably, the plate is molded as a single piece of synthetic material.

BRIEF DESCRIPTION OF THE DRAWINGS

For it to be understood correctly, the invention is again described below with reference to the appended diagrammatic drawing that represents, by way of non-limiting examples, two possible embodiments of the assembly of elements to which it relates.

DESCRIPTION OF THE PREFERRED EMBODIMENTS

Figure 1:
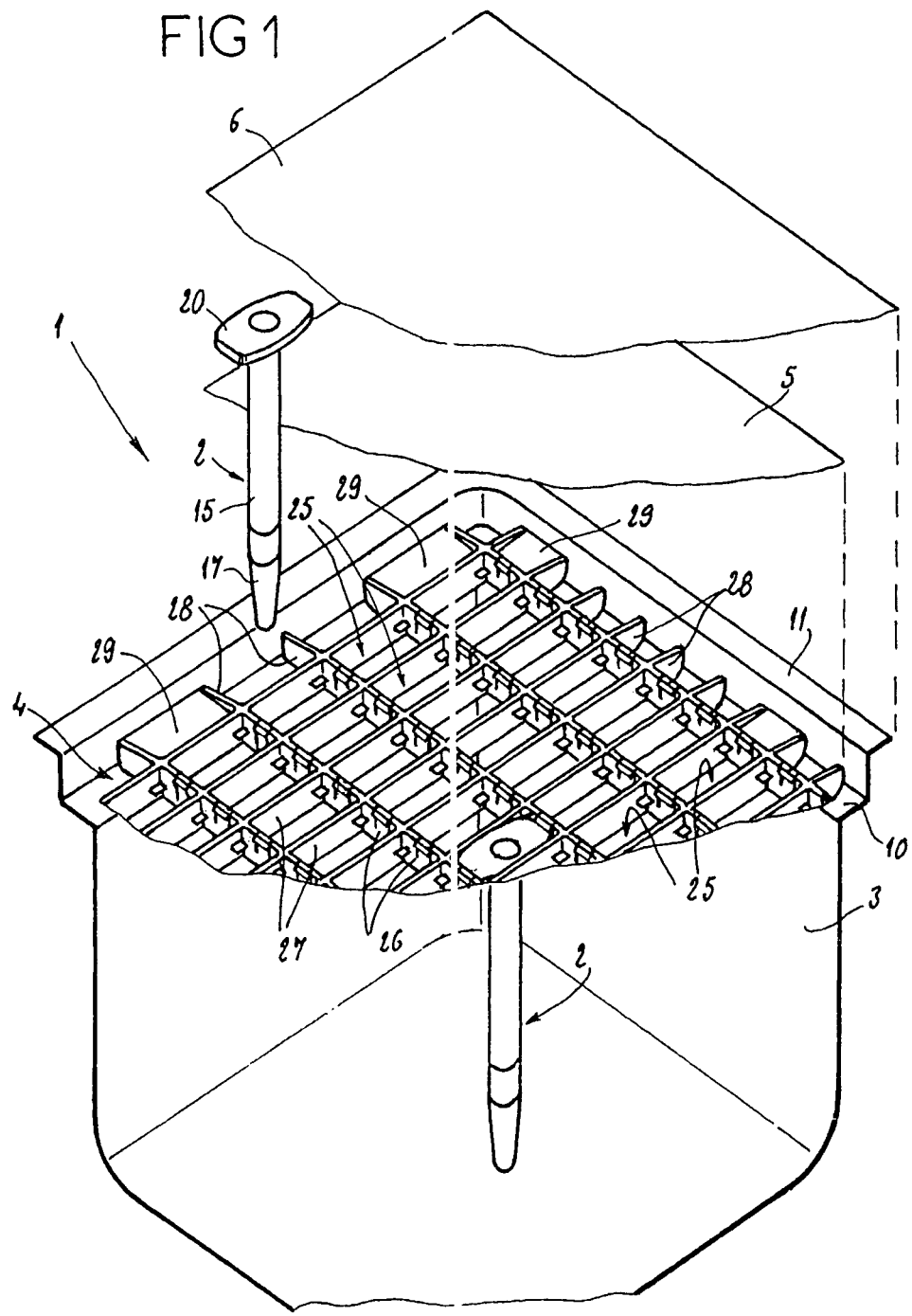
FIG. 1 is a partial view, in perspective, of a syringe-body packing box in which is placed a bulking plate forming part of this assembly of elements, according to the first embodiment.

FIG. 1 shows a packing 1 used for transporting a syringe body 2 from a site for manufacturing these syringe bodies 2 to a site for subsequent processing of these syringe bodies 2, particularly a site where they are filled.

The packing 1 comprises a box 3, a plate 4 for bulking the syringe bodies 2, a protective sheet 5 placed over the top of the plate 4 and a sealing sheet 6 closing the box 3 hermetically.

The box 3 is made from synthetic material. It comprises an upper shoulder 10 for receiving the edges of the plate 4 and an outer rim 11 allowing sealing of the sheet 6.

The plate 4 will be described in detail below.

The protective sheet 5 protects the syringe bodies 2 during subsequent operations such as sterilization, transportation and decontamination of the box 3. It may, in particular, be made from a material known as "TYVEK®", manufactured by Dupont de Nemours.

The sealing sheet 6 hermetically closes the box 3. It may also be made from "TYVEK®".

These sheets 5, 6 are permeable to gases or sterilizing radiation, but seal against bacteria.

The syringe bodies 2 conventionally comprise a hollow body 15 ending, at a distal end, in an end piece including, or capable of receiving, an injection needle, and a proximal collar 16. In the example shown in FIG. 1, the distal end of each hollow body 15 includes a cap 17 protecting the end piece and any needle, while the proximal end of this same body 15 receives, by snap-fitting on said collar, a proximal support piece 20. This proximal piece 20 allows the user's fingers to be supported on either side of the body 15 when carrying out an injection. In the example shown in FIG. 5, the syringe body 2 is engaged through an opening 22 formed in the proximal support piece 20 until the proximal collar 16 of this syringe body 2 bears against fingers of the piece 20, as will be described in greater detail below.

The plate 4 is produced by molding from a synthetic material as a single piece. As may be seen in FIG. 1, it delimits a plurality of rectangular cells 25 arranged side by side and delimited by rectilinear walls 26, 27, these walls 26, 27 intersecting at right angles and extending in terms of width in a direction perpendicular to the general plane of the plate 4. Each wall 26, 27 extends, at the edges of the plate 4, beyond the closest perpendicular wall 27, 26 in order to form tabs 28 for support holding on the shoulder 10 of the box 3. In certain locations, two consecutive tabs 28 are connected to one another by a wall 29 extending in the general plane of the plate 4, the faces of which are smooth. These walls 29 allow adhesion of the plate 4 to vacuum suction cups equipping automatic means for handling the plate 4, these handling means making it possible to seize the plate 4 with a view to its engagement in the box 3 and/or its removal from this box 3 after transportation, and/or the transfer of this plate 4 toward subsequent units for processing the syringe bodies 2, particularly units for filling these syringe bodies 2.

Figure 2:
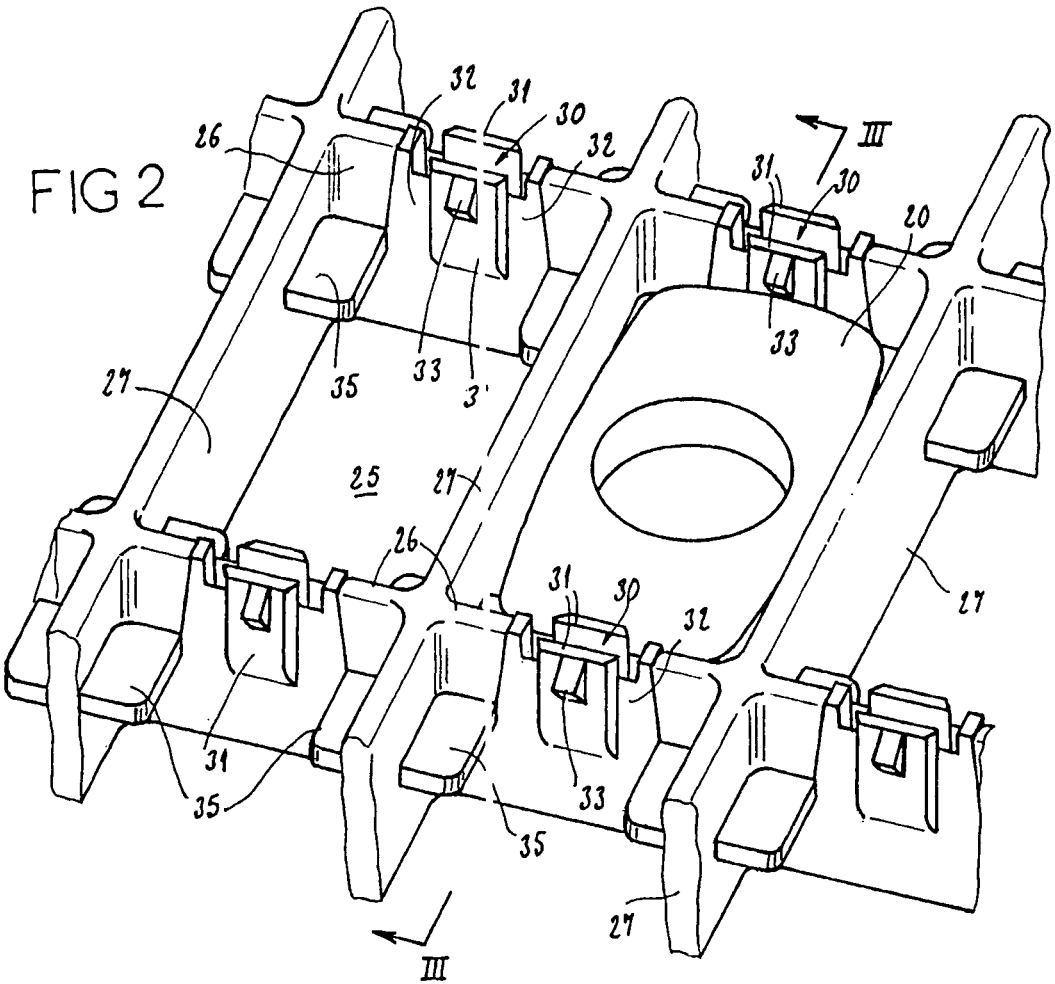
FIG. 2 is a perspective view, on a larger scale, of two cells in the bulking plate and of a proximal support piece placed in one of these cells, also forming part of said assembly of elements, this proximal support piece equipping the proximal end of a syringe body.
Figure 3:
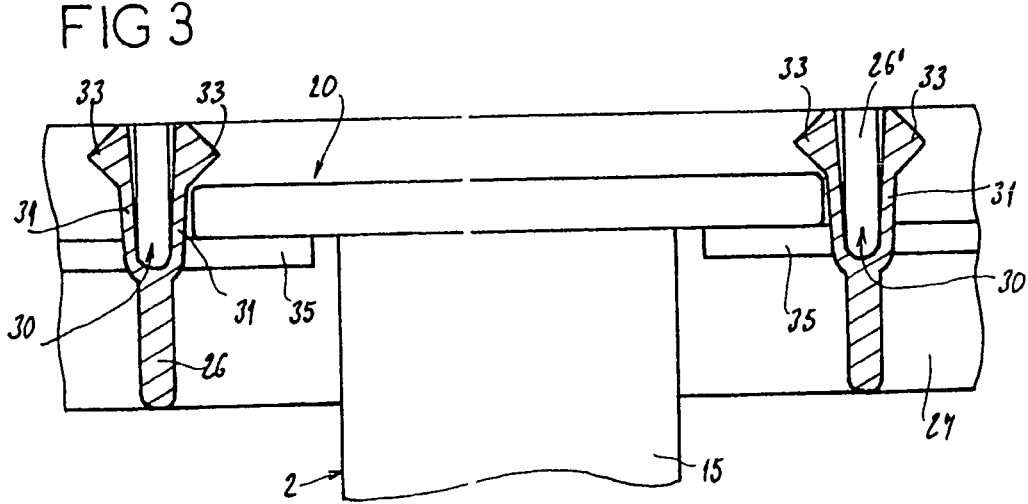
FIG. 3 is a view of the proximal support piece and of the cell receiving this piece, in section along line III-III in FIG. 2.

With reference to FIGS. 2 and 3, there are two cells 25 in the plate 4 and a syringe body 2 of which the proximal support piece 20 is engaged in a cell 25.

As may be seen in these figures, each part of a wall 26 delimiting a smaller side of a cell 25 has, in the median zone of this smaller side, a recess 30 formed in the thickness of this part of a wall 26, starting from the edge of this wall. This recess 30 delimits two snap-fitting teeth 31 connected to the contiguous edges of the wall 26 by wall sections 32.

Each snap-fitting tooth 31 is connected to the wall 26 in its lower part and comprises, on its outer face relative to the recess 30, a snap-fitting projection 33 of triangular shape. This projection 33 delimits an inclined upper edge that forms a ramp against which the piece 20 bears during its engagement in the cell 25, and a lower edge for retaining the piece 20 in the cell 25. It will easily be understood with reference to FIG. 3 that the bearing of the piece 20 up against the two opposite projections 33 of one and the same cell 25 causes the two teeth 31 to retract inside the recesses 30 in order to allow the passage of the piece 20 beyond the projections 33, the wall sections 32 allowing this withdrawal on account of their flexibility. Once the piece 20 has passed beyond the projections 33, the teeth 31 regain their normal shape shown in FIG. 3, in which the projections 33 hold the piece 20 in the cell 25.

Each cell 25 also comprises four walls 35 located at its corners, forming supports for receiving a piece 20. As shown more particularly in FIG. 3, the faces of these walls 35 turned toward the projections 33 are located at a distance from the lower zone of these projections 33 that corresponds substantially to the thickness of the lateral parts of a piece 20. The teeth 31 thus hold the piece 20 pressed against the walls 35 and therefore immobilize the syringe body 2 relative to the plate 4.

Figure 4:
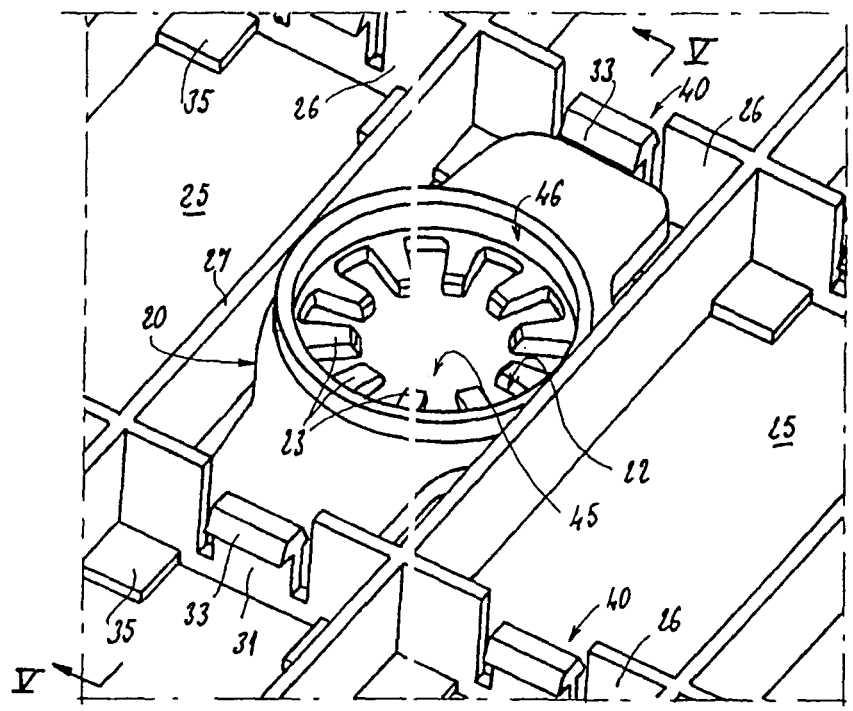
FIG. 4 is a perspective view, on a larger scale, of three cells in the bulking plate and of a proximal support piece placed in one of these cells, according to a second embodiment.
Figure 5:
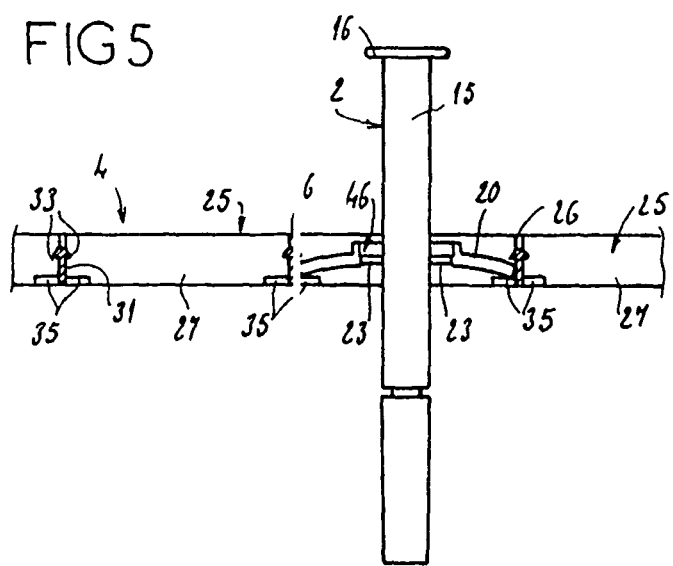
FIG. 5 is a view of the proximal support piece and of the cell receiving this piece, in section along line V-V of FIG. 4, during engagement of a syringe body through said piece.

FIGS. 4 and 5 show a plate 4 and a piece 20 that are very similar to those just described. For the purposes of simplification, the elements already described with reference to FIGS. 1 to 3, and that appear again in this plate 4 and this piece 20, will not be described again and are denoted by the same numerical references.

In this case, each wall 26 comprises a notch 40 in which there is a single snap-fitting tooth 31, this tooth 31 comprising snap-fitting projections 33 on its two opposite faces. One and the same snap-fitting tooth 31 allows the retention of two pieces 20 in two consecutive cells 25 in the longitudinal direction of these cells.

Each proximal support piece 20 comprises, as far as it is concerned, the opening 22 and the fingers 23 mentioned above. These fingers 23 project radially toward the center of this opening 22, and their free ends define a central circular passage 45 with a diameter slightly smaller than the diameter of the hollow body 15 of a syringe body 2. As will be understood with reference to FIG. 5, the piece 20 may be placed in a cell 25 by snap-fitting in the manner mentioned above, and then a syringe body 2 may be inserted in said passage 45 until the proximal collar 16 of the body 15 comes into contact with the fingers 23 and arrives in a recess 46 that the piece 20 has for this purpose. During this insertion, the fingers 23 flex and grip the body 15 between them, which assembles the support hold piece 20 and the syringe body 2 together.

It appears from the aforesaid that the invention is a decisive improvement over the prior art, providing an assembly of elements for the bulking of elongate objects, particularly syringe bodies 2, that includes a plate 4 with rigidity that is well adapted to handling operations using automated means and that has no awkward limitations in terms of its dimensions.

This assembly of elements makes it possible to immobilize the syringe bodies 2 relative to the plate 4, both in the direction of the longitudinal axis of these syringe bodies 2 and in terms of pivoting of said syringe bodies about that axis.

The assembly of elements also makes it possible to place on the syringe bodies 2, before filling, proximal support hold pieces 20, fully protecting these pieces 20 during transportation of the syringe bodies.

It goes without saying that the invention is not limited to the embodiment described above by way of example, but that it encompasses, on the contrary, all variant embodiments included in the field of protection defined by the claims appended hereto. Thus, clearly, the piece 20 shown in FIG. 4 may be used with a plate 4 as shown in FIG. 2, and a piece 20 as shown in FIG. 2 may be used with a plate 4 as shown in FIG. 4. Each snap-fitting tooth 31 shown in FIG. 4, comprising snap-fitting projections 33 on its two opposite faces, could be replaced by a pair of teeth each having a projection 33 on one of its faces, the projections 33 of these two teeth 31 being located on two opposite faces of these teeth 31. The shape of the cells may be other than rectangular, and in particular may be square, hexagonal, octagonal, or polygonal in a general manner.

The invention claimed is:

1. An assembly of elements for bulking a plurality of elongate objects, syringe bodies having an elongate axis and a support hold piece configured as a flange, comprising:
   a plate with housings for receiving the objects for bulking, each housing being delimited by lateral walls arranged to form a polygon and comprising a planar support zone having a through hole for receiving the object for bulking, the planar support zone including at least two walls arranged in a plane that is parallel to a plane of the plate;
   wherein each housing is formed by a cell;
   wherein the lateral walls delimiting the cells adjoin one another from one cell to an adjacent cell and extend in a direction substantially perpendicular to the plane of the planar support zone;
   wherein each cell is shaped in order to at least partially receive a proximal part of the object for bulking when the object for bulking extends through the through hole so that the elongate axis of the object for bulking is substantially perpendicular with respect to the plane of the planar support zone;
   wherein at least one of the lateral walls delimiting two adjacent cells comprises a recess provided in its thickness, from the section of this wall, the recess comprising snap-fitting teeth, one for each of the adjacent cells; and
   wherein a space extends between a lower region of the teeth and opposing surfaces of the at least two walls of the planar support zone, the space corresponding substantially to a thickness of the flange of the support hold piece such that the flange is immobilized when engaged in the space.

2. The assembly as claimed in claim 1, wherein each cell is dimensioned to correspond to the support hold pieces and each support hold piece is shaped to interact with the snap-fitting teeth of each cell.

3. The assembly as claimed in claim 2, wherein the lateral walls delimiting the cells are slightly flared in order to form a cell entry having dimensions greater than those of each of the support hold pieces.

4. The assembly as claimed in claim 2, wherein each support hold piece is dimensioned for being received in a cell.

5. The assembly as claimed in claim 4, wherein each support hold piece comprises an opening for the engagement of a syringe body and a series of fingers arranged radially in this opening, these fingers being shaped in order to grip the syringe body between them, with flexing, when this syringe body is engaged in said opening, in order to assemble the support hold piece and the syringe body.

6. The assembly as claimed in claim 1, wherein each cell has a square or rectangular shape.

7. The assembly as claimed in claim 6, wherein each cell comprises two immobilization means arranged on two opposite sides of the cell.

8. The assembly as claimed in claim 7, wherein each cell is rectangular and wherein the lateral walls including the recess are arranged on the smaller sides of the cell.

9. The assembly as claimed in one claim 1, wherein each support zone consists of at least one wall forming a rim extending inside the cell.

10. The assembly as claimed in claim 1, wherein the plate comprises zones allowing or promoting its gripping.

11. The assembly as claimed in claim 10, wherein said zones allowing or promoting the gripping of the plate consist of walls extending substantially in the plane of the plate, these walls forming surfaces on which vacuum suction cups equipping a machine for handling the plate may be applied.

12. The assembly as claimed in claim 1, wherein the plate is molded as a single piece of synthetic material.

13. An assembly of elements for bulking a plurality of elongate objects, the objects comprising syringe bodies having an elongate axis and a support hold piece configured as a flange, comprising:
- a plate with housings for receiving the plural objects for bulking, each housing being delimited by lateral walls arranged to form a polygon and comprising a planar support zone having a through hole for receiving the object for bulking, the planar support zone including at least two walls arranged in a plane that is parallel to a plane of the plate;
- wherein each housing is formed by a cell;
- wherein the lateral walls delimiting the cells adjoin one another from one cell to an adjacent cell and extend in a direction substantially perpendicular to the planar support zone;
- wherein each cell is shaped in order to at least partially receive a proximal part of the object for bulking when the object for bulking extends through the through hole so that the elongate axis of the object for bulking is substantially perpendicular with respect to the plane of the plate;
- wherein at least one of the lateral walls delimiting two adjacent cells comprises a notch in which there is a single snap-fitting tooth, this snap-fitting tooth comprising two snap-fitting projections on its two opposite faces, one for each of the adjacent cells; and
- wherein a space extends between a lower region of the teeth and opposing surfaces of the at least two walls of the planar support zone, the space corresponding substantially to a thickness of the flange of the support hold piece such that the flange is immobilized when engaged in the space.

14. The assembly as claimed in claim 13, wherein each cell is dimensioned to correspond to the support hold pieces and each support hold piece is shaped to interact with the immobilization means of each cell.

15. The assembly as claimed in claim 14, wherein each support hold piece is dimensioned for being received in a cell, and wherein each support hold piece comprises an opening for the engagement of a syringe body and a series of fingers arranged radially in this opening, these fingers being shaped in order to grip the syringe body between them, with flexing, when this syringe body is engaged in said opening, in order to assemble the support hold piece and the syringe body.

16. The assembly as claimed in claim 13, wherein each cell has a square or rectangular shape and comprises two immobilization means arranged on two opposite sides of the cell.

17. A storage assembly, comprising:
- a plurality of elongate objects, the objects comprising syringe bodies having an elongate axis and a support hold piece configured as a flange;
- a plate with housings for receiving the plural objects for bulking, each housing being delimited by lateral walls arranged to form a polygon and comprising a planar support zone having a through hole for receiving the object for bulking, the planar support zone including at least two walls arranged in a plane that is parallel to a plane of the plate;
- wherein each housing is formed by a cell;
- wherein the lateral walls delimiting the cells adjoin one another from one cell to an adjacent cell and extend in a direction substantially perpendicular to the plane of the planar support zone;
- wherein each cell is shaped in order to at least partially receive a respective proximal part of the object for bulking when the object for bulking extends through the through hole so that the elongate axis of the object for bulking is substantially perpendicular with respect to the plane of the planar support zone;
- wherein at least one of the lateral walls delimiting two adjacent cells comprises a recess provided in its thickness, from the section of this wall, the recess comprising snap-fitting teeth, one for each of the adjacent cells; and
- wherein a space extends between a lower region of the teeth and opposing surfaces of the at least two walls of the planar support zone, the space corresponding substantially to a thickness of the flange of the support hold piece such that the flange is immobilized when engaged in the space.

* * * * *

UNITED STATES PATENT AND TRADEMARK OFFICE
CERTIFICATE OF CORRECTION

PATENT NO. : 8,490,790 B2 Page 1 of 1
APPLICATION NO. : 10/546673
DATED : July 23, 2013
INVENTOR(S) : Cocheteux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1340 days.

Signed and Sealed this
Eighth Day of September, 2015

Michelle K. Lee
*Director of the United States Patent and Trademark Office*